United States Patent [19]

Miraki

[11] Patent Number: 5,613,949
[45] Date of Patent: *Mar. 25, 1997

[54] DOUBLE BALLOON CATHETER ASSEMBLY

[75] Inventor: Manouchehr Miraki, Aliso Viejo, Calif.

[73] Assignee: Advanced Cardiovascular Systems, Inc., Santa Clara, Calif.

[*] Notice: The term of this patent shall not extend beyond the expiration date of Pat. No. 5,549,554.

[21] Appl. No.: 222,145

[22] Filed: Apr. 1, 1994

[51] Int. Cl.$^6$ .................................................. A61M 29/00
[52] U.S. Cl. .......................... 604/101; 604/283; 604/284
[58] Field of Search .............................. 604/94, 96, 101, 604/167, 283, 284; 606/192, 196, 199

[56]  References Cited

U.S. PATENT DOCUMENTS

| | | | |
|---|---|---|---|
| 3,516,408 | 6/1970 | Montanti | 604/284 |
| 3,937,224 | 2/1976 | Uecker . | |
| 4,230,119 | 10/1980 | Blum . | |
| 4,425,124 | 1/1984 | Womack | 604/94 |
| 4,447,227 | 5/1984 | Kotsanis . | |
| 4,475,898 | 10/1984 | Brodner et al. | 604/9 |
| 4,705,502 | 11/1987 | Patel . | |
| 4,731,055 | 3/1988 | Melinyshyn et al. . | |
| 4,734,094 | 3/1988 | Jacob et al. . | |
| 4,751,924 | 6/1988 | Hammerschmidt . | |
| 4,753,238 | 6/1988 | Gaiser . | |
| 4,769,017 | 9/1988 | Fath | 604/283 |
| 4,771,777 | 9/1988 | Horzewski et al. . | |
| 4,834,710 | 5/1989 | Fleck | 604/163 |
| 4,840,690 | 6/1989 | Melinyshyn et al. . | |
| 4,902,273 | 2/1990 | Choy | 604/101 |
| 4,911,163 | 3/1990 | Fina . | |
| 4,943,277 | 7/1990 | Bolling . | |
| 4,973,305 | 11/1990 | Goltzer . | |
| 5,002,532 | 3/1991 | Gaiser et al. . | |
| 5,102,390 | 4/1992 | Crittenden et al. . | |
| 5,129,883 | 7/1992 | Black . | |
| 5,152,277 | 10/1992 | Honda et al. . | |
| 5,158,540 | 10/1992 | Wijay et al. . | |
| 5,163,906 | 11/1992 | Ahmadi . | |
| 5,176,638 | 1/1993 | Don Michael . | |
| 5,188,596 | 2/1993 | Condon et al. . | |
| 5,203,771 | 4/1993 | Melker | 604/283 |
| 5,213,577 | 5/1993 | Kratzer . | |
| 5,217,439 | 6/1993 | McClusky | 604/163 |
| 5,222,941 | 6/1993 | Don Michael . | |
| 5,226,889 | 7/1993 | Sheiban . | |
| 5,234,411 | 8/1993 | Vaillancourt | 604/163 |
| 5,256,141 | 10/1993 | Gencheff et al. . | |
| 5,348,542 | 9/1994 | Ellis | 604/283 |

FOREIGN PATENT DOCUMENTS

| | | |
|---|---|---|
| 0277370 | 8/1988 | European Pat. Off. . |
| 0277367 | 8/1988 | European Pat. Off. . |
| 0277367A1 | 10/1988 | European Pat. Off. . |
| 0341988 | 11/1989 | European Pat. Off. . |
| 0362146 | 4/1990 | European Pat. Off. . |
| 0369012 | 5/1990 | European Pat. Off. . |
| 0402467 | 12/1990 | European Pat. Off. . |
| 0412664 | 2/1991 | European Pat. Off. . |
| 0309469 | 3/1991 | European Pat. Off. . |
| 0421031 | 4/1991 | European Pat. Off. . |
| 0427429 | 5/1991 | European Pat. Off. . |

(List continued on next page.)

Primary Examiner—Corrine M. McDermott
Assistant Examiner—Chalin Smith
Attorney, Agent, or Firm—Heller Ehrman White & McAuliffe

[57] ABSTRACT

A double balloon dilatation catheter assembly comprises an elongate catheter body terminating at two opposing distal ends. Each distal end comprises one dilatation balloon provided thereon for dilating a stenosis. The catheter body further comprises a central portion which communicates with two separate delivery passages. Each delivery passage operates to deliver inflation media from an inflation port located in the catheter body central portion to a dilatation balloon to inflate the balloon. A connector may be slidably positioned along the catheter body central portion for allowing the delivery of inflation media from an external source through the inflations ports and to the dilatation balloons.

14 Claims, 8 Drawing Sheets

FOREIGN PATENT DOCUMENTS

| | | |
|---|---|---|
| 0474906 | 3/1992 | European Pat. Off. . |
| 0476855A1 | 3/1992 | European Pat. Off. . |
| 2254351 | 7/1975 | France . |
| 2380033 | 9/1978 | France . |
| 2437841 | 4/1980 | France . |
| 2545360 | 9/1984 | France . |
| 2454589 | 6/1975 | Germany . |
| 2412553 | 9/1975 | Germany . |
| 2848484 | 9/1982 | Germany . |
| 1113896 | 5/1968 | United Kingdom . |
| 2243553 | 11/1991 | United Kingdom . |
| 2245499 | 9/1992 | United Kingdom . |
| WO89/01309 | 2/1989 | WIPO . |

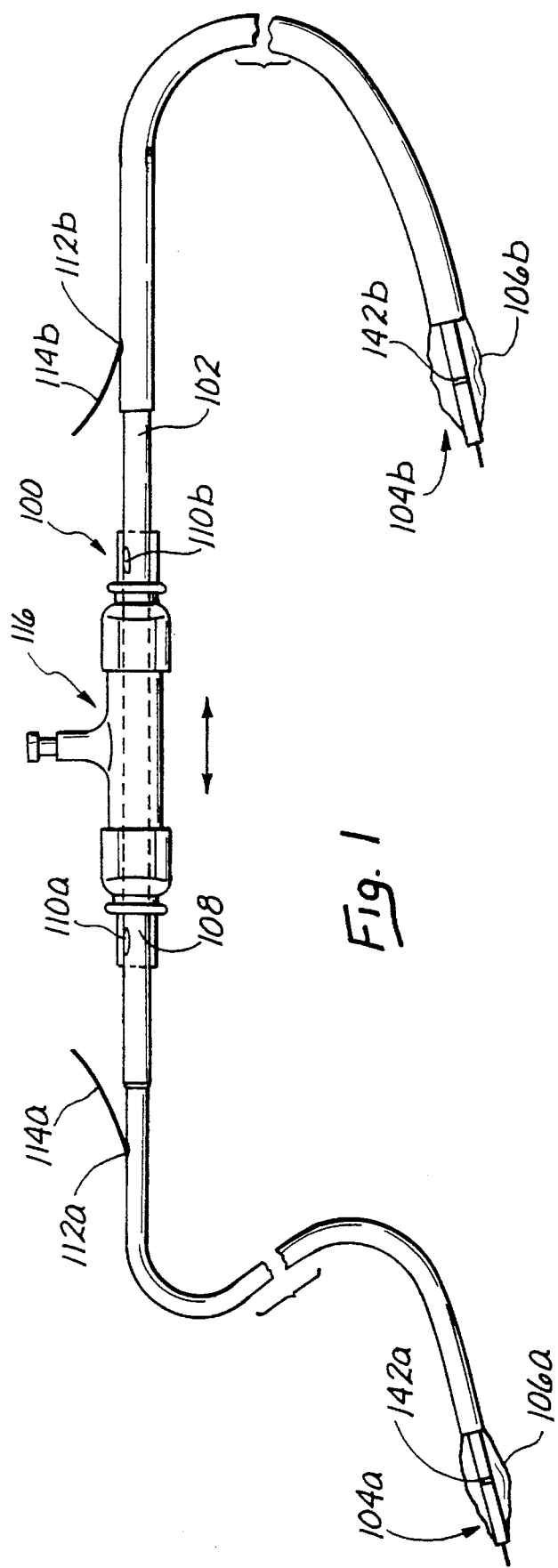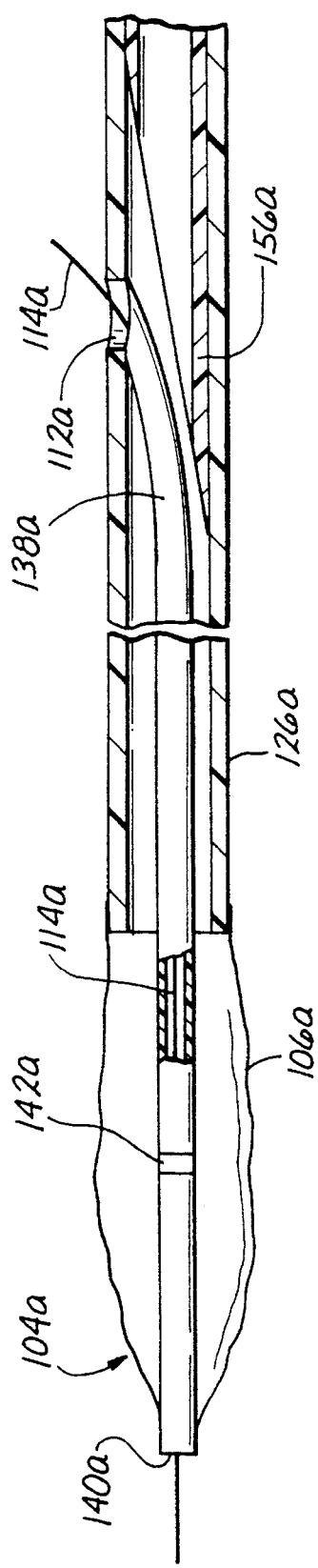

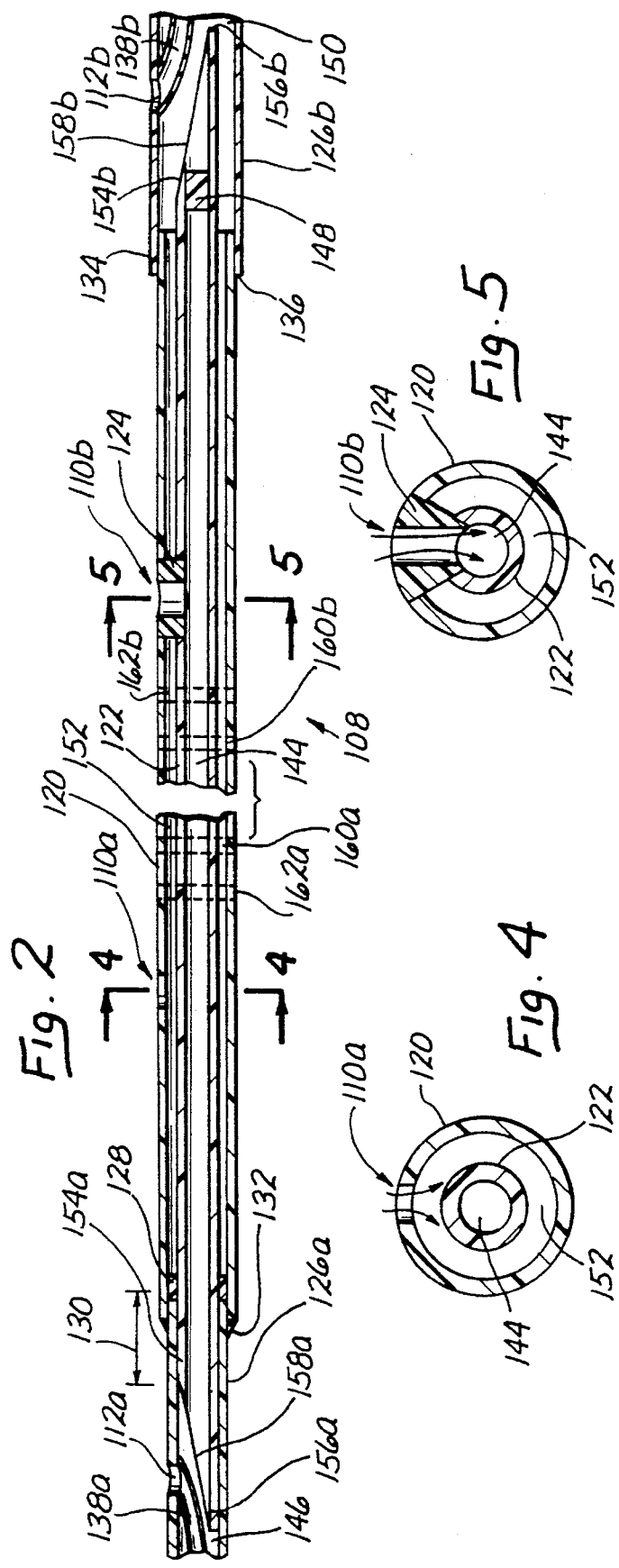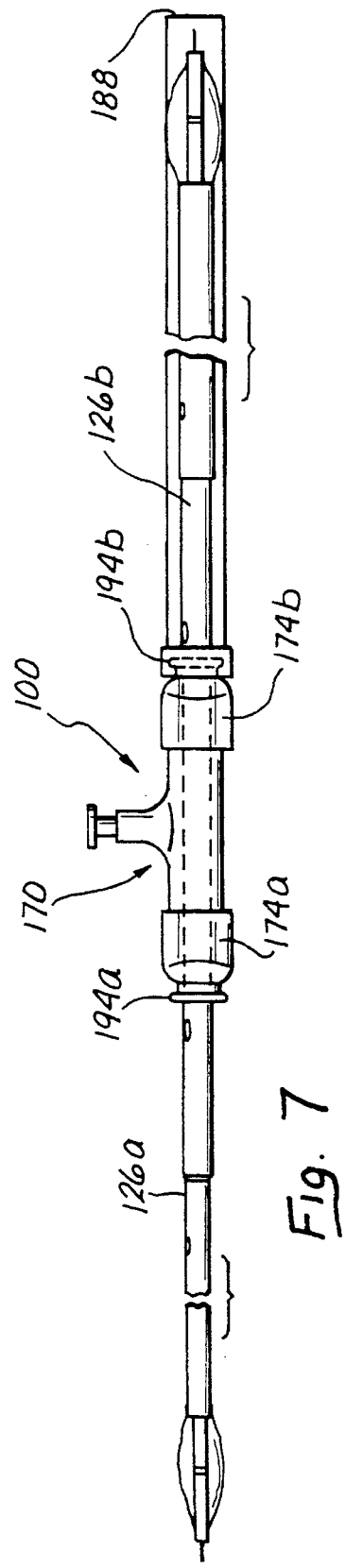

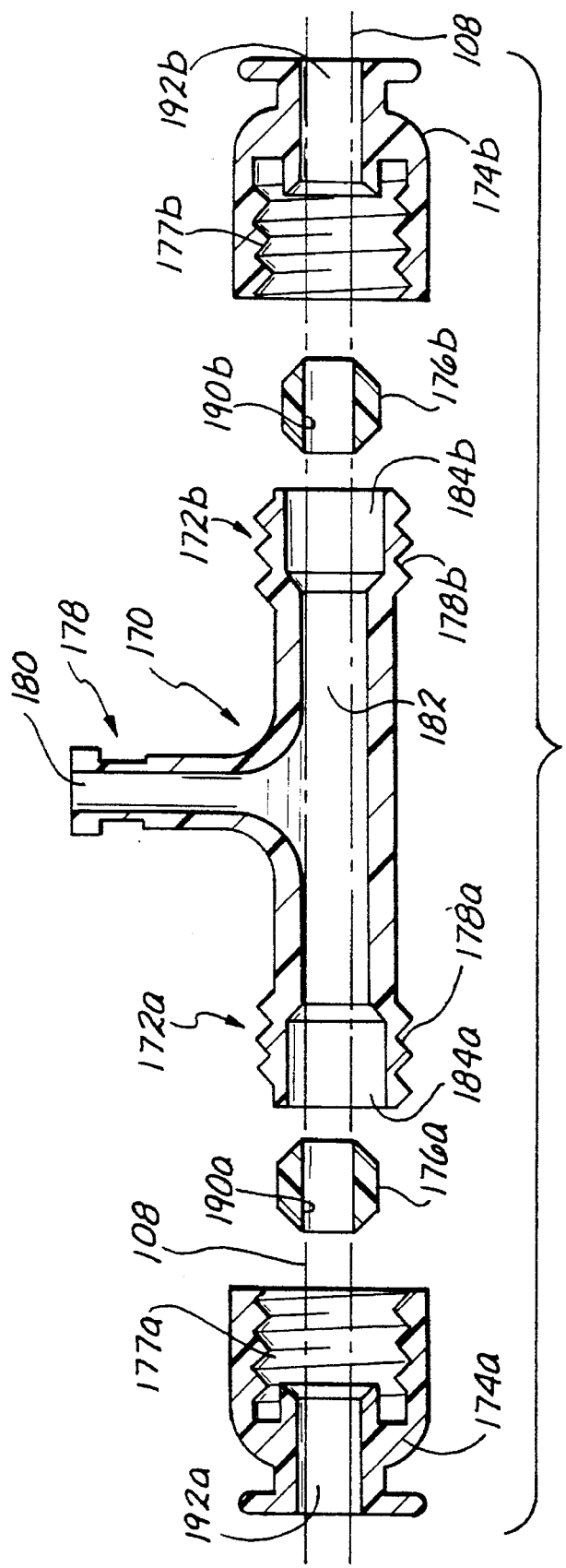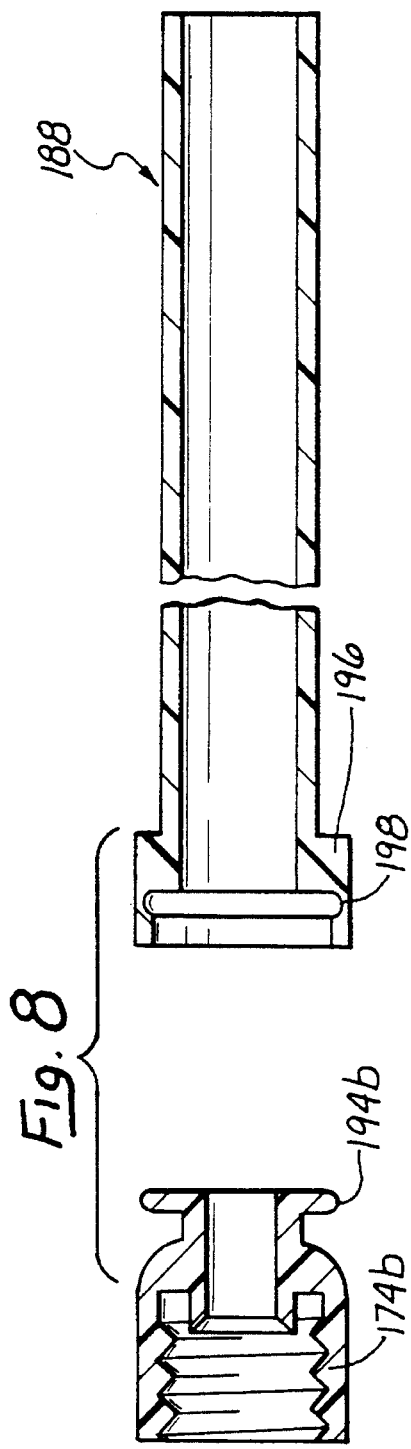

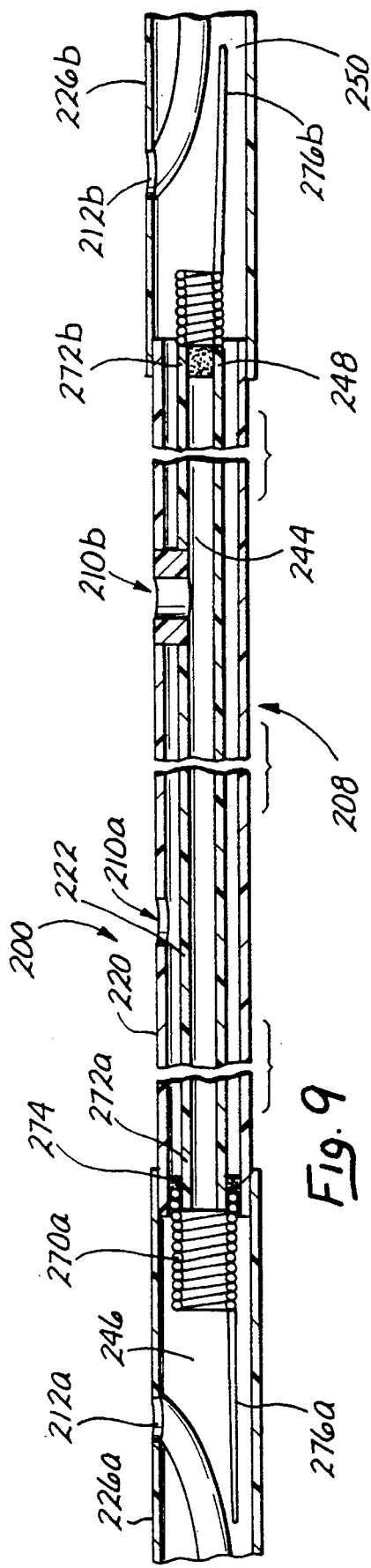
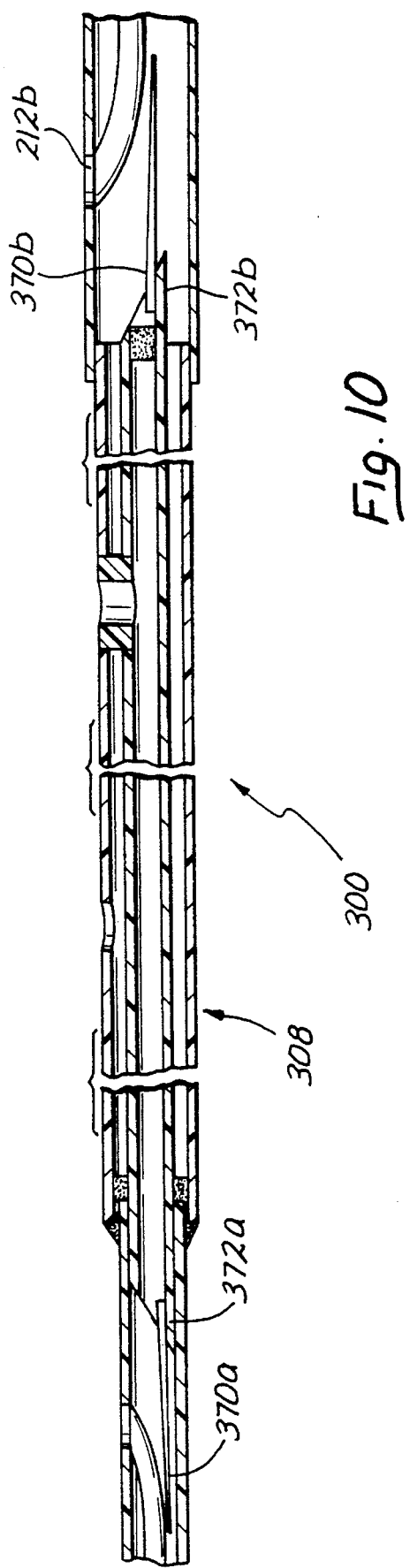
Fig. 9
Fig. 10

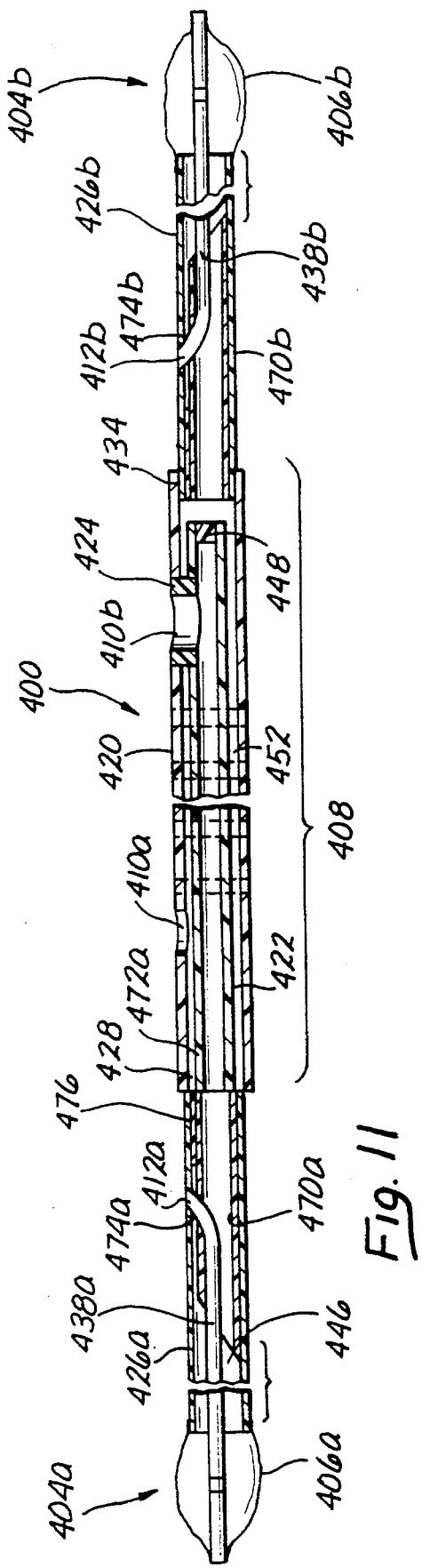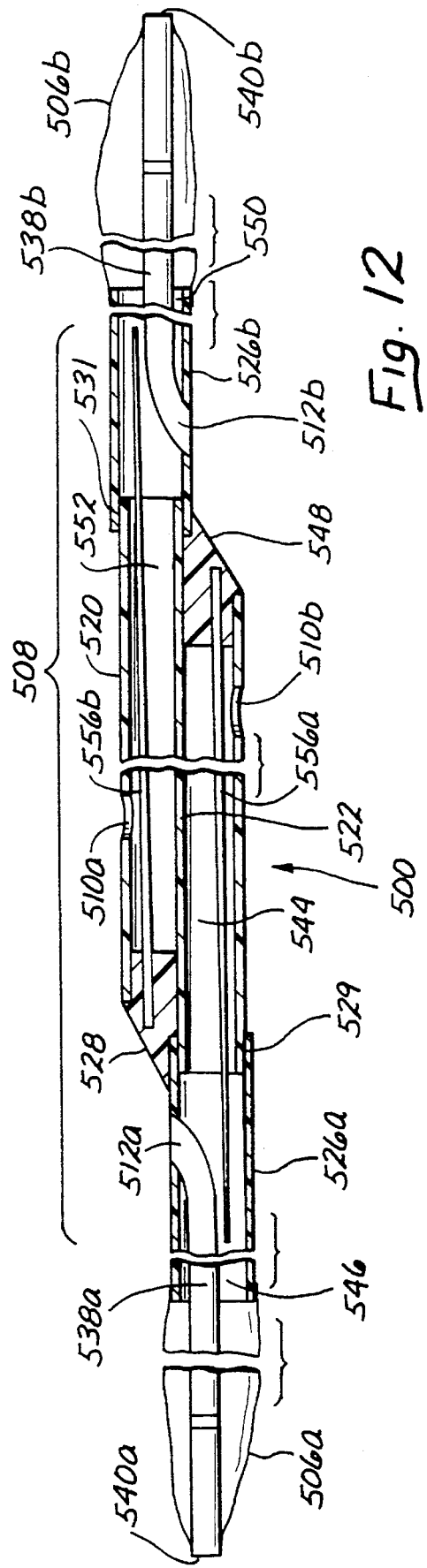

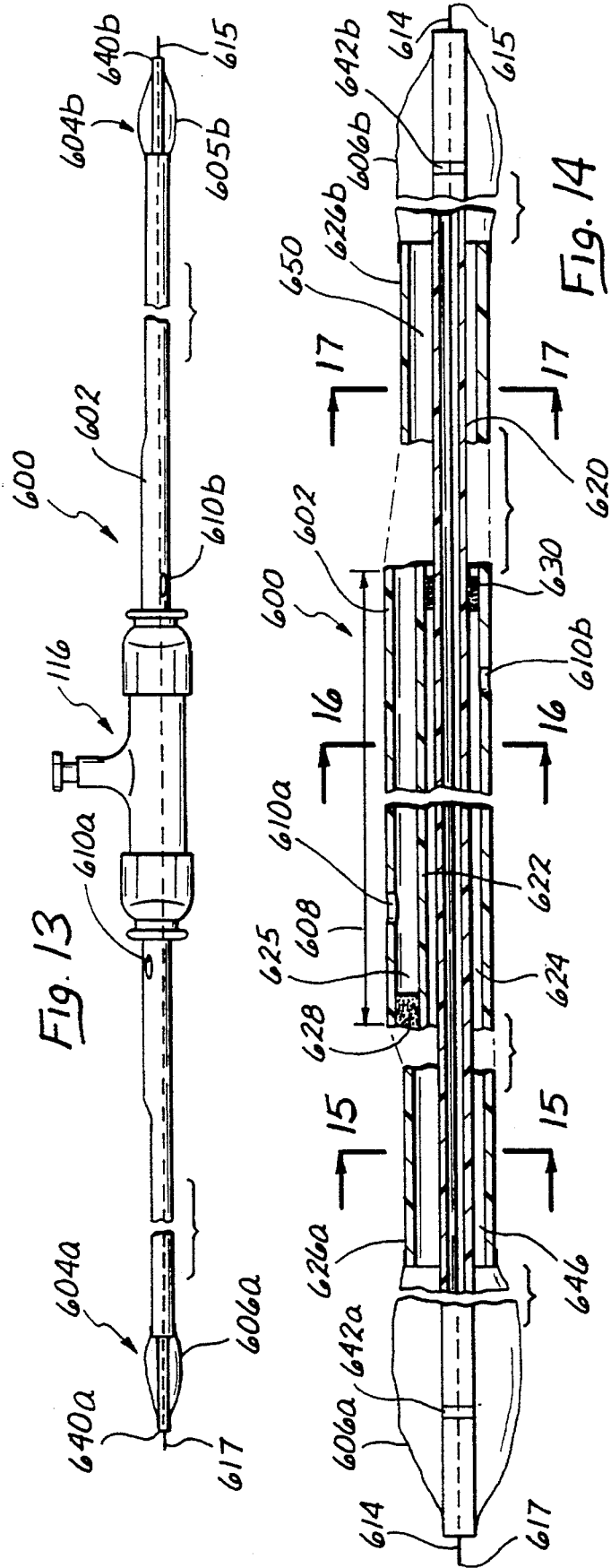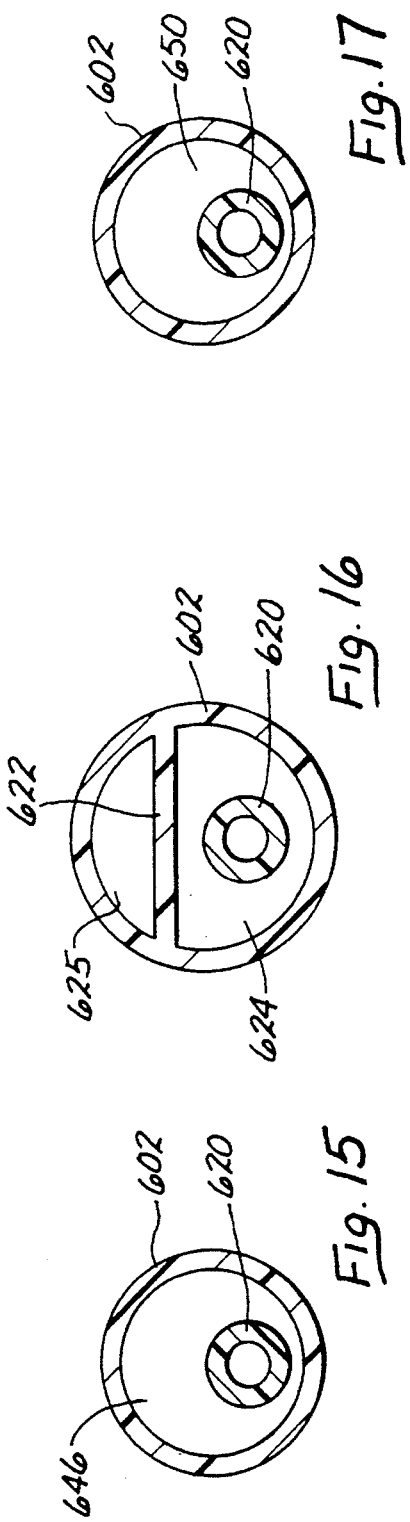

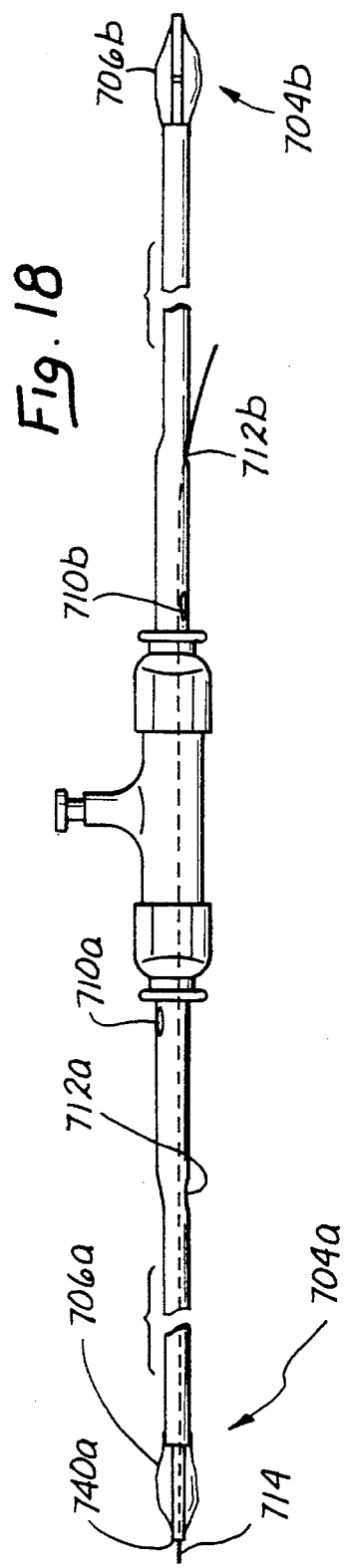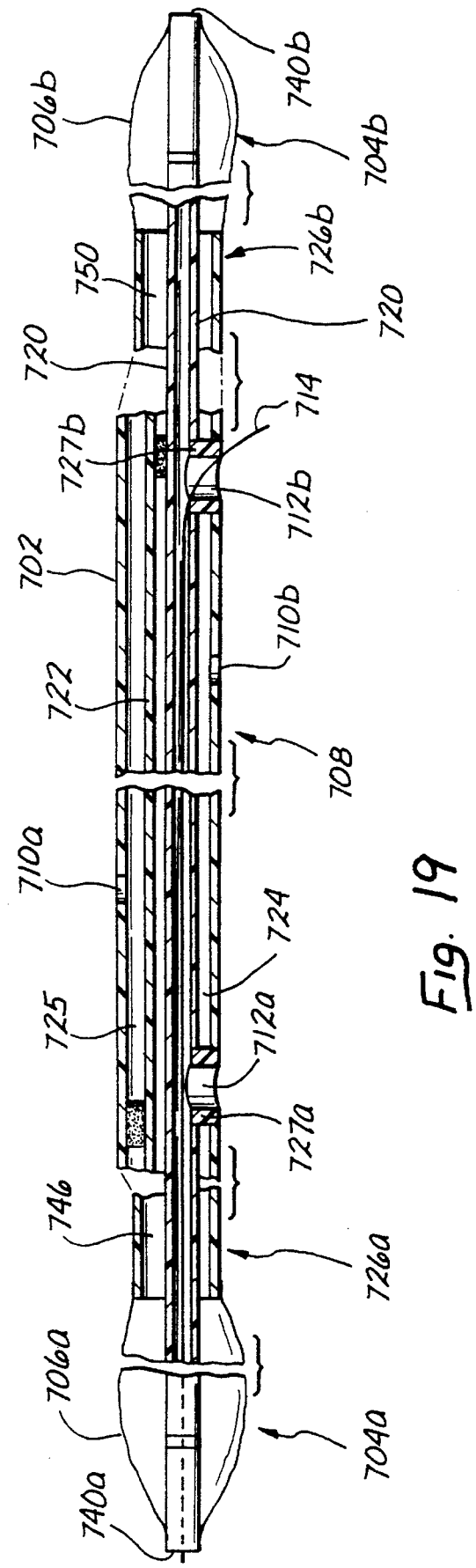

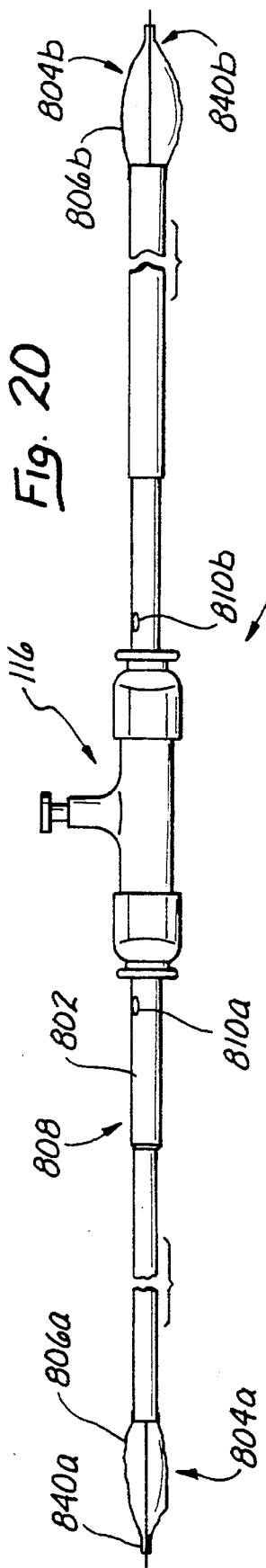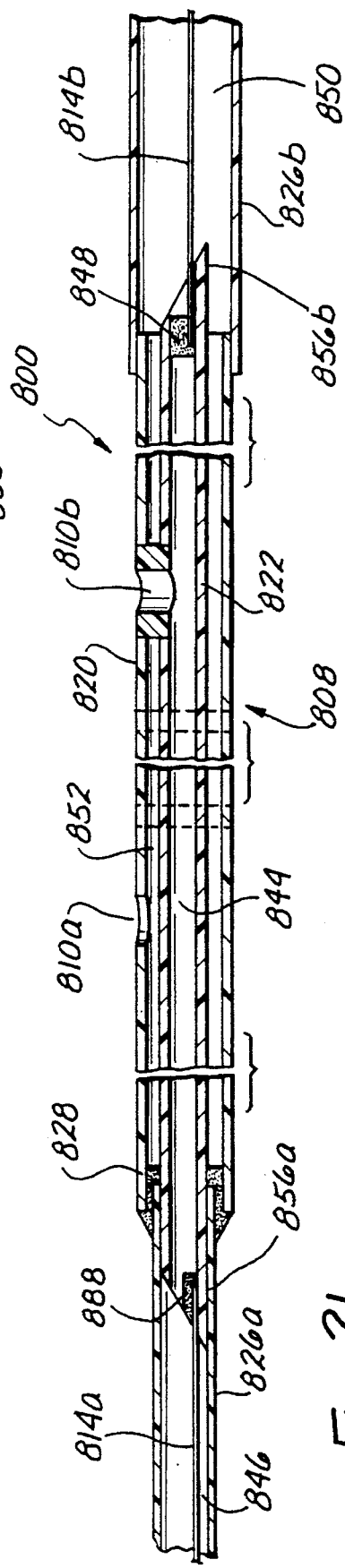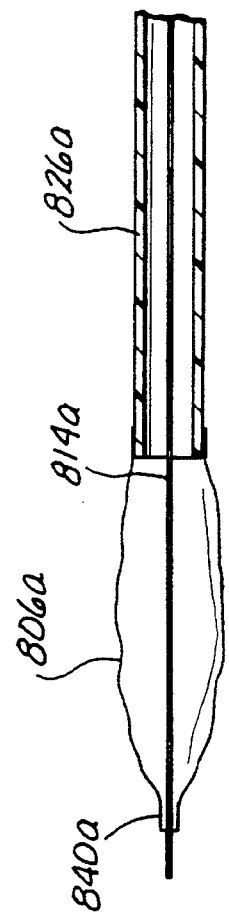

DOUBLE BALLOON CATHETER ASSEMBLY

FIELD OF THE INVENTION

The present invention relates in general to the field of dilatation or balloon catheters employed in the treatment of vascular diseases. More particularly, the present invention relates to a double balloon catheter assembly which has dilatation balloons provided on opposite ends of the catheter assembly and a connector assembly that can be slidably positioned along the catheter body for introducing inflation media into either balloon. The double balloon catheter assembly allows the same catheter assembly to used when balloon exchange is to be effected.

BACKGROUND OF THE INVENTION (i) Angioplasty and Conventional Dilatation Catheter Systems.

Over the last decade the medical procedure known as angioplasty has become widely accepted as a safe and effective method for treating various types of vascular diseases. For example, angioplasty is widely used for opening stenoses throughout the vascular system and particularly for opening stenoses in coronary arteries. At present, the most common form of angioplasty is called percutaneous transluminal coronary angioplasty (PTCA). This procedure utilizes a dilatation catheter having an inflatable balloon at its distal end. Using a fluoroscope and radiopaque dyes for visualization, the distal end of the dilatation catheter is guided into position through a guide catheter and across the stenosis and the balloon is inflated for a brief duration to open the artery and establish adequate blood flow. Typically, inflation of the balloon is accomplished by supplying pressurized fluid through an inflation lumen in the catheter which is connected to an inflation apparatus located outside the patient's body. Conversely, applying a negative pressure to the inflation lumen collapses the balloon to its minimum dimension for initial placement or removal of the balloon catheter within the target blood vessel.

A number of balloon catheter designs have been developed which have contributed to the safety and acceptability of PTCA and similar medical procedures. The most common design is known as an "over-the-wire" balloon catheter. This device typically utilizes a relatively large lumen for passage of a guide wire and injection of angiographic visualization dye to assist in the placement of the device. In some cases, a second parallel lumen is provided for inflation and deflation of the balloon, such a design commonly referred to as a "dual lumen" design. Alternatively, instead of a second lumen, the wall of the catheter body itself defines an open space between the catheter body and the guidewire lumen for allowing inflation media to pass therethrough. This is commonly referred to as a "coaxial" design. Typically, a steerable guide wire is positioned within the larger lumen and the entire assembly is maneuvered into an initial position within the target artery through a previously positioned large diameter guide catheter. Once near the site of the stenoses the guide wire can be rotated and axially extended or retracted into position across the lesion. The catheter is subsequently advanced along the guide wire to position its balloon end across the lesion prior to inflation of the balloon and dilatation of the stenosis.

An alternative over-the-wire catheter assembly utilizes a non-removable or fixed guide wire that allows for longitudinal or axial movement. However, this design has a significant drawback because the entire non-removable guide wire catheter assembly must be removed to accomplish replacement or exchange of the balloon. In some cases of PTCA it is necessary to replace the balloon with one of different diameter or configuration following the initial dilatation. Additionally, cases of acute reclosure have been noted where the lesion recloses following dilatation and removal of the balloon catheter. This alternative system increases the difficulties of these subsequent procedures by requiring that the replacement catheter renegotiate the entire placement path without the advantage of a guide wire.

A "monorail" or "rapid exchange" variant of the standard balloon-over-a-wire system also has been developed where only the distal portion of the balloon catheter tracks over the guide wire. This system utilizes a conventional inflation lumen and a relatively short guiding or through lumen at the distal end. Its principal benefits are the reduction of frictional drag over the length of the externally located guide wire and the ease of balloon exchange. It provides the ability to recross an acutely closed vessel or to exchange balloons without removing the guide wire.

Another dilatation catheter design is the "fixed-wire" or integrated "balloon-on-a-wire" dilatation catheter. These single lumen designs utilize a relatively narrow wire positioned within the inflation lumen and permanently fixed to the distal end of the balloon. This produces a low-profile assembly which is able to cross severely narrowed lesions and to navigate tortuous vascular pathways. Additionally, the fixed guide wire bonded at the distal end of the balloon improves the steerability and pushability of these designs which enhances their maneuverability. The thin shaft design also improves coronary visualization and enables all but the tightest critical lesions to be crossed. However, though able to provide relatively quick and simple balloon placement as well as providing access to lesions otherwise unsuitable for PTCA, fixed-wire systems sacrifice the ability to maintain guide wire position across the lesion when exchanging balloons or the safety advantage of being able to recross an acutely closed vessel without repositioning the entire assembly.

(ii) The Need for Catheter Exchange.

In many angioplasty procedures, it may become necessary to exchange catheters. There are many reasons which may require such catheter exchange. For example, the balloon catheter may malfunction, a larger balloon may be required to further dilate the vascular stenoses, another device may be needed to remove vascular material, and so on. In each of these situations, the original dilatation catheter must be removed, and a new dilatation catheter must be used. It is estimated that about half of the angioplasty procedures require the use of more than one dilatation catheter.

The use of two or more dilatation catheters significantly increases the cost to both the patient and the hospital. For example, the patient must pay for the cost of an additional dilatation catheter; the hospital must stock a larger inventory of dilatation catheters, which requires more storage space; and more packaging components are required, which increases the amount of waste or recyclable matter. All the above factors also result in greater administrative attention and expense.

Thus, there remains a need for a dilatation catheter assembly that is cost-efficient, is easy to use, and is easy to manufacture.

SUMMARY OF THE INVENTION

These and other objects are achieved by the double balloon catheter assembly of the present invention which, in accordance with broad structural aspects thereof, comprises an elongate body which in turn comprises a first distal end and a second distal end. The first and second distal ends are coupled to a central portion, the first and second distal ends further having first and second dilatation balloons, provided at the respective ends. The first and second distal ends are comprised of a flexible catheter body.

The elongate catheter body further comprises first delivery means provided in the central portion and the first distal end and communicating with the first dilatation balloon for delivering an inflation media to the first dilatation balloon to inflate the first balloon. The first delivery means further comprises a first inflation port provided in the central portion. The elongate catheter body also comprises second delivery means provided in the central portion and the second end and communicating with the second dilatation balloon for delivering an inflation media to the second dilatation balloon to inflate the second balloon. The second delivery means further comprises a second inflation port provided in the central portion.

In addition, the double balloon catheter assembly according to the present invention further includes a connector assembly slidably positioned about the central portion of the elongate body and adapted to be secured at the locations of the first inflation port and the second inflation port. The connector assembly is adapted to provide inflation media from an inflation source to the first and second delivery means through the first and second inflation ports. A protective sheath is coupled to the connector assembly to cover the distal end that is not in use.

In a "rapid-exchange" embodiment of the present invention, guidewire ports are provided at the respective distal ends and communicate with guidewire lumens which extend through respective distal openings at the distal ends. The delivery means includes hypo-tube passageways provided in the central portion and communicating with the respective flexible catheter bodies of the distal ends and the inflation ports, with appropriate seals provided to prevent inflation media from flowing to the other flexible distal catheter body (i.e., the one not in use).

In an "over-the-wire" embodiment of the present invention, a guidewire lumen extends from one distal opening through the elongate body to the other distal opening. The delivery means includes passageways provided in the central portion and communicating with the respective flexible catheter bodies of the distal ends and the inflation ports, with appropriate seals provided to prevent inflation media from flowing to the other flexible distal catheter body (i.e., the one not in use).

In a "long monorail over-the-wire" embodiment of the present invention, the operation principles of "over-the-wire" and "rapid-exchange" catheters may be interchangeably used. Two guidewire ports are provided adjacent opposite ends of the central portion and communicate with a guidewire lumen which extends from one distal opening through the elongate body to the other distal opening. When the guidewire extends through the guidewire port closer to the distal end being used, the catheter system operates under the principles of a "rapid-exchange" catheter. On the other hand, when the guidewire extends through the guidewire port farther away from the distal end being used, the catheter system operates under the principles of an "over-the-wire" catheter. This catheter system can be operated under either principle, and also facilitates convenient guidewire exchange while keeping the dilatation balloon positioned at the site of the stenosis.

In a "fixed-wire" embodiment of the present invention, guidewires are affixed to the central portion and extend through each distal end. The delivery means includes hypo-tube passageways provided in the central portion and communicating with the respective flexible catheter bodies of the distal ends and the inflation ports, with appropriate seals provided to prevent inflation media from flowing to the other flexible distal catheter body (i.e., the one not in use).

The principles of the present invention also relate to a method of performing an angioplasty procedure to dilate a stenosis located in a vessel inside a patient. The method comprises the step of providing a catheter assembly according to the embodiments described above and elsewhere in the detailed description of the invention below. The method further includes the steps of positioning the connector assembly over the location of the first inflation port, and then inserting the first end of the catheter assembly into a patient's vessel and advancing the first end in the vessel until the first dilatation balloon is positioned across a stenosis. Inflation media is then delivered through the first inflation port and the first delivery means to inflate the first dilatation balloon.

When catheter exchange is required, the first end of the catheter assembly is withdrawn from the patient's vessel. The method then includes the steps of positioning the connector assembly over the location of the second inflation port, and inserting the second end of the catheter assembly into a patient's vessel and advancing the second end in the vessel until the second dilatation balloon is positioned across the same stenosis. Inflation media is then delivered through the second inflation port and the second delivery means to inflate the second dilatation balloon. At the end of the procedure, the second end of the catheter assembly is withdrawn from the patient's vessel.

In this manner, the present invention provides two easy-to-use catheter systems on the same catheter assembly, thereby allowing angioplasty and catheter exchange to be performed economically, quickly, and conveniently while retaining all the necessary safety precautions. The cost reduction is achieved by providing one catheter assembly instead of two separate catheters, which also results in fewer disposable materials, and less inventory and lower administrative costs for the hospitals.

Other features and advantages of the present invention will become apparent from the following detailed description, taken in conjunction with the accompanying drawings which illustrate, by way of example, the principles of the present invention.

BRIEF DESCRIPTION OF THE DRAWINGS

FIG. 1 is a perspective view of a double balloon catheter assembly according to a "rapid exchange" version of the present invention.

FIG. 2 is an enlarged cross-sectional view of a central portion of a first embodiment of the present invention according to the "rapid exchange" catheter assembly of FIG. 1.

FIG. 3 is a cross-sectional view of a first distal end of the catheter assembly of FIGS. 1 and 2.

FIG. 4 is a cross-sectional view of a portion of the catheter assembly of FIG. 2 taken along line 4—4 thereof.

FIG. 5 is a cross-sectional view of a portion of the catheter assembly of FIG. 2 taken along line 5—5 thereof.

FIG. 6 is an exploded cross-sectional view of an exemplary connector assembly that may be used with the catheter assembly of FIG. 2.

FIG. 7 is a perspective view of the catheter assembly of FIG. 1 illustrating the use of protective sheath at an unused distal end thereof.

FIG. 8 is an exploded cross-sectional view of the catheter assembly of FIG. 7 showing how the sheath is engaged to the connector assembly thereof.

FIG. 9 is an enlarged cross-sectional view of a central portion of a second embodiment of the present invention according to the "rapid exchange" catheter assembly of FIG. 1.

FIG. 10 is an enlarged cross-sectional view of a central portion of a third embodiment of the present invention according to the "rapid exchange" catheter assembly of FIG. 1.

FIG. 11 is an enlarged cross-sectional view of a portion of a fourth embodiment of the present invention according to the "rapid exchange" catheter assembly of FIG. 1.

FIG. 12 is an enlarged cross-sectional view of a central portion of a fifth embodiment of the present invention according to the "rapid exchange" catheter assembly of FIG. 1.

FIG. 13 is a perspective view of a sixth embodiment of the present invention according to an "over-the-wire" version of the catheter assembly.

FIG. 14 is an enlarged cross-sectional view of a central portion of the catheter assembly of FIG. 13.

FIG. 15 is a cross-sectional view of a portion of the catheter assembly of FIGS. 13 and 14 taken along line 15—15 thereof.

FIG. 16 is a cross-sectional view of a portion of the catheter assembly of FIGS. 13 and 14 taken along line 16—16 thereof.

FIG. 17 is a cross-sectional view of a portion of the catheter assembly of FIGS. 13 and 14 taken along line 17—17 thereof.

FIG. 18 is a perspective view of a seventh embodiment of the present invention according to an "over-the-wire" version of the catheter assembly.

FIG. 19 is an enlarged cross-sectional view of a central portion of the catheter assembly of FIG. 18.

FIG. 20 is a perspective view of an eighth embodiment of the present invention according to a "fixed-wire" version of the catheter assembly.

FIG. 21 is an enlarged cross-sectional view of a central portion of the catheter assembly of FIG. 20.

FIG. 22 is a cross-sectional view of a first distal end of the catheter assembly of FIGS. 20 and 21.

DETAILED DESCRIPTION OF THE PREFERRED EMBODIMENTS

The present invention is directed generally to a double balloon dilatation catheter assembly. The catheter assembly comprises an elongate catheter body terminating at both ends. For the purposes of the present invention, both ends of the catheter body shall be referred to as "distal" ends. Each distal end of the catheter body comprises one dilatation balloon provided thereon for dilating a stenosis. The catheter body further comprises a central portion which communicates with two separate delivery means. Each delivery means operates to deliver inflation media from an inflation port located in the catheter body central portion to a dilatation balloon to inflate the balloon. A connector may be slidably positioned along the catheter body central portion for allowing the delivery of inflation media from an external source through the inflation ports and to the dilatation balloons.

In operation, during a normal angioplasty procedure, a first distal end and its balloon of the double balloon catheter assembly may be used to access the site of a stenosis. If a new balloon is needed, the first distal end of the catheter assembly is withdrawn from the patient's vasculature and the second distal end and its balloon may then inserted therein and advanced to the site of the stenosis.

The present invention will be described in accordance with the various versions of dilatation catheters, namely, the "rapid-exchange" "over-the-wire" and "fixed-wire" versions, and in accordance with different embodiments thereof. In this regard, it will be appreciated by those skilled in the art that the basic principles of the present invention may be embodied by any of the "rapid-exchange", "over-the-wire" and "fixed-wire" versions of dilatation catheters, and that other embodiments, alternatives and modifications may be made without departing from the spirit and scope of the present invention.

1. "Rapid-Exchange" Versions

Referring to FIG. 1, the "rapid-exchange" version of the present invention is denoted by the numeral 100 and comprises an elongate catheter body 102 that has two opposing ends, a first distal end 104a and a second distal end 104b. A first dilatation balloon 106a is provided at the first distal end 104a, while a second dilatation balloon 106b is provided at the second distal end 104b. The catheter body 102 further comprises a central portion 108, and inflation ports 110a and 110b are provided along the central portion 108. Each inflation port is initially sealed by a protective layer (not shown) of material to prevent blood or other materials from entering therethrough prior to use. This protective layer is preferably made from the same material as the balloon. Guidewire ports 112a and 112b are provided distal to the inflation ports 110a and 110b for allowing guidewires 114a and 114b to be inserted through the respective distal ends 104a and 104b of the catheter assembly 100. A connector assembly 116 is slidably positioned along the central portion 108 and operates in the manner described hereinbelow.

a. A First Embodiment

In a first embodiment of the present invention illustrated in FIGS. 2–5, the central portion 108 comprises an outer hypo-tube 120 and an inner hypo-tube 122. The hypo-tubes are preferably made from stainless steel or a kink-resistant alloy such as nickel titanium. The inner hypo-tube 122 is positioned inside the outer hypo-tube 120, and is connected to the outer hypo-tube 120 by soldering or welding 124 at the location of the inflation port 110b. Each end of the outer hypo-tube 120 is connected to a separate distal catheter body which is actually inserted into a patient's vasculature. The distal catheter body is preferably made of a flexible material such as polyethylene, polypropylene, marlex, or any other conventional catheter material as is well-known in the art.

For example, one end of the outer hypo-tube 120 is connected to the inner hypo-tube 122 at radial connection 128. The connection 128 may be created by soldering, welding, laser-welding or brazing the outer hypo-tube 120 to the proximal end of the first distal catheter body 126a. The first distal catheter body 126a is radially bonded to the inner hypo-tube 122 along radial bond area 130. Taper 132 is made of polyethylene or adhesive and are formed adjacent the connection 128. Another end of the outer hypo-tube 120 is connected to a second distal catheter body 126b at radial connections 134. The connection 134 may be created by heat bonding the outer hypo-tube 120 to the proximal end of the second distal catheter body 126b. Similarly, taper 136 is also made of polyethylene or adhesive and are formed adjacent the connection 134.

Guidewire ports 112a and 112b are provided in close proximity to the connections 128 and 134. Guidewire ports 112a and 112b communicate with respective guidewire lumens 138a and 138b which extend to respective distal openings (for example, see 140a in FIG. 3) at the distal ends 104a and 104b. Guidewires 114a and 114bmay be inserted through the guidewire lumens 138a and 138b and extended beyond the distal ends 104a and 104b, respectively.

Radiopaque markers 142a and 142b function to provide the implanting physician with a readily apparent visual reference which can be viewed on a fluoroscope during the angioplasty procedure. During positioning of the apparatus the physician simply manipulates the guidewire 114a until the appropriate marker 142a, 142b is positioned directly adjacent or across the stenosis. Because of its positioning on guidewire 114a relative to balloon 106a, when marker 142a is so positioned, balloon 106a is positioned across the stenosis as well.

Accordingly, the above-described structure of the central portion 108 defines two passages for the delivery of inflation media to the respective balloons 106a and 106b. For instance, the passage for delivery of inflation media to balloon 106a is defined by the inflation port 110b and the lumen 144 of the inner hypo-tube 122 which communicates with the lumen 146 of the first distal catheter body 126a. The proximal or rear end of the lumen 144 is sealed at 148 by soldering, welding, or laser-welding to prevent inflation media from escaping into the lumen 150 of the second distal catheter body 126b. Similarly, the passage for delivery of inflation media to balloon 106b is defined by the inflation port 110a and the lumen 152 of the outer hypo-tube 120 which communicates with the lumen 150 of the second distal catheter body 126b. The proximal or rear end of the lumen 152 is sealed at connection 128 in the manner described above to prevent inflation media from escaping into the lumen 146 of the first distal catheter body 126a.

The inner hypo-tube 122 is configured such that the hypo-tube wall adjacent the guidewire ports 112a and 112b, such as at 154a and 154b, terminate at locations which are proximal to the guidewire ports 112a and 112b, while the hypo-tube wall opposite the guidewire ports 112a and 112b, such as at 156a and 156b, terminate at locations which are distal to the guidewire ports 112a and 112b. In other words, both ends the inner hypo-tube 122 are cut diagonally along imaginary lines 158a and 158b such that the hypo-tube wall opposite the guidewire ports 112a and 112b, such as at 156a and 156b, extend beyond the guidewire ports 112a and 112b. This configuration for the inner hypo-tube 122 provides the flexible catheter body 126a and 126b with a degree of flexibility, yet provides sufficient rigidity to the areas of the catheter body around the guidewire ports 112a and 112b to protect against kinking when a guidewire is exited from either of the guidewire ports 112a or 112b.

Additionally, the central portion 108 is provided with brachial markers 160a and 160b, and femoral markers 162a and 162b, which are used to locate the distance of the catheter assembly 100 with respect to the guiding catheter.

b. A Connector Assembly and Sheath For Use With All Embodiments

A connector assembly 116 that is adapted for use with all embodiments of the present invention is illustrated in FIG. 6. The connector assembly 116 comprises a Y-connector 170 having two ends 172a and 172b, with a tightening mechanism secured to each end 172a and 172b. Each tightening mechanism comprises a compression fitting 174a, 174b and an O-ring or grommet 176a, 176b.

More specifically, the Y-connector 170 comprises an inflation arm 178 having an internal passage 180 which communicates with a bi-directional inflation channel 182. The O-rings or grommets 176a, 176b have openings 190a, 190b, and the compression fittings 174a, 174b are provided with channels 192a, 192b. Each end 172a and 172b has an opening 184a, 184b, respectively, which is adapted to receive an O-ring or grommet 176a, 176b. The compression fittings 174a, 174b are provided with internal threads 177a, 177b which may be threadably engaged with the threads 178a, 178b at both ends 172a, 172b of the Y-connector 170. The central portion 108 of the catheter body 102 may be received within the inflation channel 182 of the Y-connector 170, the openings 190a, 190b of the O-rings or grommets 176a, 176b, and the channels 192a, 192b of the compression fittings 174a, 174b, so that the combined connector assembly 116 can slide along the catheter body 102.

In operation, the compression fittings 174a, 174b are loosely secured to the ends 172a, 172b of the Y-connector 170. This loose connection is achieved by minimally engaging the threads 177a and 178a, and 177b and 178b, so that the O-rings or grommets 176a, 176b positioned at the ends 172a, 172b are not compressed, thereby maintaining the openings 190a and 190b at a wider diameter. This allows the central portion 108 to slide freely in both directions to be positioned at a particular location. When the desired location has been reached, such as where the inflation channel 182 is positioned over an inflation port 110a or 110b, the compression fittings 174a, 174b are tightened by turning to further engage the threads 177a and 178a, and 177b and 178b. This tightening compresses the O-rings or grommets 176a, 176b so that they tightly grip the catheter body 102. This secures the connector assembly 116 at that particular location so that an inflation media can be injected through the internal passage 180 and the inflation channel 182 into the inflation port 110a or 110b. When the connector assembly 116 needs to be moved to another location, the compression fittings 174a, 174b are loosened and the connector assembly 116 advanced.

Referring now to FIG. 7, a protective sheath 188 may be fitted over the unused distal catheter body, which in this case is the second distal catheter body 126b. Referring to FIG. 8, each compression fitting 174a, 174b has a flange 194a or 194b that extends radially at the tip thereof. The sheath 188 has a-bulbous receiving end 196 with a radial well 198 adapted to receive and engage the flange 194a or 194b of the compression fitting 174a or 174b. This engagement secures the sheath 188 to a compression fitting 174a or 174b.

c. A Second Embodiment

A second embodiment 200 according to the present invention is illustrated in FIG. 9. The structure and configuration of the central portion 208 of the catheter assembly 200 are substantially the same as those for the catheter assembly 100 of FIGS. 2–5. However, the opposite ends of the inner hypo-tube 222 are not diagonally cut; instead, each opposite end has a helical coil brazed or connected thereto.

Specifically, a first helical coil 270a is connected to a first end 272a of the inner hypo-tube 222 at radial connection 274 by soldering, welding, laser welding or other conventional means. The first helical coil 270a may be formed by coiling a wire, and leaving one elongate end 276a of the wire uncoiled and tapered such that it extends in the lumen 246 of the first distal catheter body 226a to a location distal of the guidewire port 212a. Like the extended hypo-tube wall in the catheter assembly 100, the elongate end 276a also operates to prevent kinking. The wire of the helical coil 270a may be made from stainless steel.

Similarly, a second helical coil 270b is connected to a second end 272b of the inner hypo-tube 222. The uncoiled and tapered elongate end 276b of the helical coil 270b extends in the lumen 250 of the second distal catheter body 226b to a location distal of the guidewire port 212b, and operates to prevent kinking. The lumen of the inner hypo-tube 222 is likewise sealed at 248 by soldering, welding, laser welding, or other conventional means.

d. A Third Embodiment

A third embodiment 300 according to the present invention is illustrated in FIG. 10. The structure and configuration of the central portion 308 of the catheter assembly 300 is substantially the same as those for the catheter assembly 100. However, the opposite ends of the inner hypo-tube 322 further include a tapered wire connected thereto to prevent kinking.

Specifically, a first tapered wire 370a is brazed or connected to a first end 372a of the inner hypo-tube 322 to prevent kinking. Similarly, a second tapered wire 370b is brazed or connected to a second end 372b of the inner hypo-tube 322, and also operates to prevent kinking. The ends 372a and 372b are shown as being diagonally cut in a manner similar to that for the catheter assembly 100, but may also be provided without the diagonal cut.

e. A Fourth Embodiment

A fourth embodiment 400 according to the present invention is illustrated in FIG. 11. The structure and configuration of the central portion 408 of the catheter assembly 400 is substantially the same as those for the catheter assembly 100. However, additional segments of hypo-tube 470a and 470b are provided at the opposite ends of the inner hypo-tube 422.

Specifically, a hypo-tube segment 470a is brazed or connected to a first end 472a of the inner hypo-tube 422 and the outer hypo-tube 420 at radial connection 428. The hypo-tube segment 470a may be made from stainless steel, and extends into the lumen 446 of the first distal catheter body 426a beyond the location of the guidewire port 412a. The hypo-tube may be coated with polyethylene to enhance bonding. The hypo-tube segment 470a is further heat bonded or adhesive bonded at radial bond 476 to the distal catheter body 426a, such radial bond also operating to seal the lumen 452 of the outer hypo-tube 420. An opening 474a is provided in the hypo-tube segment 470a for receiving the guidewire lumen 438a. The hypo-tube segment 470a therefore operates to prevent kinking. An identical hypo-tube segment 470b is connected at radial connection 434 to the outer hypo-tube 420 and provided to extend through the second distal catheter body 426b.

f. A Fifth Embodiment

A fifth embodiment 500 according to the present invention is illustrated in FIG. 12. In the catheter system 500, the central portion 508 is comprised of a flexible double-lumen tube instead of a hypo-tube. The flexible double-lumen tube is preferably made from a flexible material such as polyethylene, polypropylene, marlex, or other conventional materials.

Referring to FIG. 12, the central portion 508 comprises an outer tube 520 that has its internal lumen divided by a dividing wall 522 into two separate lumens, 544 and 552. The first distal catheter body 526a is connected to the outer tube 520 by heat or adhesive bonding at location 529, and connected to the dividing wall 522 by heat bonding and seal 528. Likewise, the second distal catheter body 526b is connected to the outer tube 520 by heat or adhesive bonding at location 531, and connected to the dividing wall 522 by head bonding and seal 548. A first inflation port 510a communicates with the lumen 552 of the outer tube 520 and the lumen 550 of the second distal catheter body 526b to deliver inflation media to the balloon 506b. A second inflation port 510b communicates with the lumen 544 of the outer tube 520 and the lumen 546 of the first distal catheter body 526a to deliver inflation media to the balloon 506a. The seal 528 seals the lumen 552 to prevent inflation media from leaking out thereat, and also connects the outer tube 520 to the dividing wall 522. Likewise, the seal 548 seals the lumen 544 to prevent inflation media from leaking out thereat, and connects the outer tube 520 to the dividing wall 522.

Guidewire ports 512a and 512b are provided in the distal catheter bodies 526a and 526b, respectively, to communicate with guidewire lumens 538a and 538b, respectively. Opposing tapered wires 556a and 556b are provided in the separate lumens 544 and 552, respectively, and they both extend to a point beyond or distal of the respective guidewire port 512a or 512b. The wires 556a and 556b therefore operate to prevent kinking.

The distal catheter bodies 526a and 526b may also be made from the same material as the outer tube 520 and the dividing wall 522, or may be made from any other conventional soft material.

g. Operation of the "Rapid Exchange" Double Balloon Catheter Assemblies

The "rapid exchange" double-balloon catheter assemblies 100, 200, 300, 400, and 500 described hereinabove may be operated or used in the same manner. Therefore, description of the operation will be limited only to the catheter assembly 100 shown in FIGS. 2–5; those skilled in the art will appreciate that the same operating principles apply to the other assemblies 200, 300, 400 and 500.

During a normal angioplasty procedure, a guidewire 114a is first inserted into a patient's artery through a guiding catheter (not shown), and advanced until the guidewire tip is positioned across a stenosis. The protective layer is removed from inflation port 110b, and the connector assembly 116 is then advanced along the central portion 108 so that it is positioned over the inflation port 110b. The compression fittings 174a, 174b of the connector assembly 116 are then tightened to secure the connector assembly 116 in place over the inflation port 110b. After the first distal catheter body 126a has been primed from any air, it is then inserted into the artery by inserting the proximal end of the guidewire 114a through the distal opening 140a (see FIG. 3) so that the proximal end of the guidewire 114a passes through the guidewire port 112a. The first distal catheter body 126a is then advanced along the artery to the location of the stenosis. An inflation media is introduced through the internal passage 180 and inflation channel 182 of the connector assembly 116 and the inflation port 110b and into the lumen 144 of the inner hypo-tube 122. The inflation media then passes through the lumen 146 of the first distal catheter body 126a to inflate the balloon 106a to dilate or redistribute the stenosis.

If a replacement or new balloon is needed, then the balloon 106a is deflated and withdrawn from the artery while maintaining the guidewire 114a in the same position. The protective sheath 188 is removed from the second distal catheter body 126a, and the protective layer removed from inflation port 110a. The compression fittings 174a, 174b are loosened so that the connector assembly 116 can be moved from its position over the inflation port 110b and advanced along the central portion 108 to be positioned over the inflation port 110a. The compression fittings 174a, 174b of the connector assembly 116 are then tightened to secure it in place over the inflation port 110a. After the second distal catheter body 126b has been primed, the catheter assembly 100 is then reversed so that the second distal catheter body 126b is inserted into the artery by inserting the proximal end of the guidewire 114a through the distal opening 140b so that the proximal end of the guidewire 114a passes through the guidewire port 112b. The second distal catheter body 126b is then advanced along the artery to the location of the stenosis. An inflation media is introduced through the connector assembly 116, the inflation port 110a and into the lumen 152 of the outer hypo-tube 120. The inflation media then passes through the lumen 150 of the second distal catheter body 126b to inflate the balloon 106b to dilate or redistribute the stenosis. At the end of this procedure, the second distal catheter body 126b may be withdrawn.

Thus, the same catheter assembly 100 can be used when a larger balloon is needed. This allows the physician to save previous time by not needing to open the packaging for a new catheter since the physician merely reverses the catheter assembly 100 and uses the other catheter body. This also saves the hospital and the patient money since the cost of a new catheter will not need to be incurred.

It is possible to provide both the first and second distal catheter bodies 126a and 126b with balloons of different sizes. This is because a common reason for exchanging or replacing a new catheter is because a balloon of a different size is needed. It is also possible to provide both the first and second distal catheter bodies 126a and 126b with different diameters. This is because the different diameters result in different deflation times depending on balloon size.

2. "Over-The-Wire" Version

Referring to FIG. 13, the "over-the-wire" version of the present invention is denoted by the numeral 600 and comprises an elongate catheter body 602 that has two opposing ends, a first distal end 604a and a second distal end 604b. A first dilatation balloon 606a is provided at the first distal end 604a, while a second dilatation balloon 606b is provided at the second distal end 604b. The catheter body 602 further comprises a central portion 608, and inflation ports 610a and 610b are provided along the central portion 608. A guidewire 614 (see FIG. 14) is adapted to pass through the entire catheter body 602 and through distal openings 640a and 640b provided at the distal ends 604a and 604b. A connector 116 is slidably positioned along the central portion 608 and operates in the manner described above.

In a sixth embodiment of the present invention illustrated in FIGS. 14–17, the entire catheter body 602 is comprised of a flexible material such as polyethylene, marlex, polypropylene, braided polyethylene tubing, polyamide, hypo-tube, or other similar conventional material. The flexible catheter body 602 comprises an inner guidewire lumen 620 which extends across the entire length of the catheter body 602. At a first distal catheter section 626a and a second distal catheter section 626b, the catheter body 602 and the guidewire lumen 620 define internal passages 646 and 650, respectively, which allow inflation media to flow therethrough to the balloons 606a and 606b (see FIGS. 15 and 17). However, at the central portion 608, the catheter body 602 further defines a dividing wall 622 which divides the internal passage into a first inflation passage 624 which communicates with the internal passage 646 and a second inflation passage 625 which communicates with the internal passage 650 (see FIG. 16). Inflation port 610a communicates with inflation passage 625 and internal passage 650 to deliver inflation media to balloon 606b, while inflation port 610b communicates with inflation passage 624 and internal passage 646 to deliver inflation media to balloon 606a. The inflation passage 625 is sealed at 628 by soldering, welding, laser welding, heat bonding or other conventional sealing means. Likewise, the inflation passage 624 is sealed radially at 630 by the same sealing means.

In operation, the connector assembly 116 is advanced along the central portion 608 so that it is positioned over the inflation port 610b. The compression fittings 174a, 174b of the connector assembly 116 are then tightened to secure the connector assembly 116 in place over the inflation port 110b. The first distal catheter body 626a is primed with inflation media, and a guidewire 614 is inserted through the length of the guidewire lumen 620. The combined first distal catheter body 626a and guidewire 614 are then inserted into a patient's artery through a guiding catheter (not shown), and advanced until the guidewire tip is adjacent a stenosis. An inflation media is introduced through the internal passage 180 and inflation channel 182 of the connector assembly 116, and the inflation port 610b, into the first inflation passage 624, and through the internal passage 646, to inflate the balloon 606a to dilate or redistribute the stenosis.

If a replacement or larger balloon is needed, then a guidewire extension (not shown) is connected or "docked" to the proximal end of the guidewire 614 which extends out of the distal opening 640b. Examples of guidewire extension systems and their operations are shown in U.S. Pat. No. 5,271,415, issued on Dec. 21, 1993, and U.S. Pat. No. 5,282,478, issued on Feb. 1, 1994, the disclosures of which are hereby entirely incorporated herein by this reference. The entire catheter assembly 600 is then withdrawn from the artery along the guidewire 614 and the guidewire extension while keeping the distal tip of the guidewire 614 at the location of the stenosis. The compression fittings 174a, 174b are loosened so that the connector assembly 116 can be moved from its position over the inflation port 610b and advanced along the central portion 608 to be positioned over the inflation port 610a. The compression fittings 174a, 174b of the connector assembly 116 are then tightened to secure it in place over the inflation port 610a. After the second distal catheter body 626b has been primed, the catheter assembly 600 is then reversed so that the second distal catheter body 626b is inserted into the artery by advancing it along the guidewire extension and the guidewire 614, and along the artery to the location of the stenosis. An inflation media is introduced through the connector assembly 116 and the inflation port 610a into the second inflation passage 625, and then through the internal passage 650, to inflate the balloon 606b to dilate or redistribute the stenosis. At the end of this procedure, the second distal catheter body 626b may be withdrawn.

3. The "Long-Monorail Over-The-Wire" Version

The seventh embodiment 700 of the present invention is illustrated in FIGS. 18 and 19. This catheter assembly 700 embodies principles of both the "rapid-exchange" or "monorail" catheter and the "over-the-wire" catheter, and is therefore called the "long-monorail over-the-wire" version. In this regard, the structure and configuration of the catheter assembly 700 is substantially similar to that of the "over-the-wire" catheter assembly 600. However, the guidewire path is modified so that the guidewire does not extend across the entire length of the catheter body from one distal opening to the other. Instead, the guidewire is inserted through a guidewire port in the central portion of the catheter assembly 700, much like in the "rapid-exchange" embodiments described above.

Specifically, guidewire ports 712a and 712b are provided at about the opposite ends of the central portion 708 by heat bonding or soldering at locations 727a and 727b. Otherwise, the structure of the inner guidewire lumen 720, the first and second distal catheter sections 726a and 726b, the internal passages 746 and 750, and the dividing wall 722 which divides the internal passage into a first inflation passage 724 and a second inflation passage 725, are essentially the same as those corresponding elements in the catheter assembly 600 shown in FIGS. 13–17.

When the first distal end 704a is to be used, the proximal end of guidewire 714 is inserted through distal opening 740a and advanced along guidewire lumen 720 until it exits at guidewire port 712b. The combined catheter assembly 700 with its guidewire 714 is then inserted into an artery and advanced to the site of the stenosis. Since this guidewire 714 extends along the length of the first distal catheter body 726a and the central portion 708, the operation would be similar to that of an "over-the-wire" catheter. That is, to accomplish catheter exchange, a guidewire extension must be connected to the proximal end of the guidewire 714 in the manner described above for the "over-the-wire" catheter assembly 600 before the catheter assembly 700 is withdrawn. The catheter assembly 700 is then re-inserted into the artery through its second distal end 704b and the guidewire port 712a.

The structural configuration of the catheter assembly 700, and in particular, the provision of the guidewire ports 712a and 712b, also allows the physician with the flexibility of using the catheter assembly 700 in a "rapid-exchange" method. For example, when the first distal end 704a is to be inserted into the artery, the guidewire 714 may be inserted through the guidewire port 712a so that the catheter assembly 700 may be operated like a "rapid-exchange" catheter. Likewise, when the second distal end 704b is to be inserted into the artery, the guidewire 714 may be inserted through the guidewire port 712b.

Furthermore, when being used as a "rapid-exchange" catheter, the guidewire ports 712a and 712b allow for convenient guidewire exchange without losing the location of the original guidewire. Guidewire exchange may be required in certain situations, such as when an original guidewire fails. Specifically, to exchange guidewires when the first distal end 704a has been inserted into the artery with the guidewire 714 extending through the guidewire port 712a, the guidewire 714 is withdrawn from the catheter body while the first distal end 704a remains across the stenosis with the balloon 706a in an uninflated condition. Since the first distal end 704a and the guidewire port 712a are still inside the patient's vessel, a replacement guidewire may be inserted through the guidewire port 712b and advanced to the location of the stenosis. Likewise, to exchange guidewires when the second distal end 704b has been inserted into the artery with the guidewire 714 extending through the guidewire port 712b, a replacement guidewire may be inserted through the guidewire port 712a and advanced to the location of the stenosis.

Thus, the catheter assembly 700 may be adapted conveniently for use as "over-the-wire" and "rapid-exchange" catheters, whichever method the physician prefers. The catheter assembly 700, when used as a "rapid-exchange" catheter, also facilitates convenient guidewire exchange.

4. The "Fixed-Wire" Version

Referring to FIGS. 20–22, the "fixed-wire" version of the present invention is denoted by the numeral 800 and comprises an elongate catheter body 802 that has two opposing ends, a first distal end 804a and a second distal end 804b. A first dilatation balloon 806a is provided at the first distal end 804a, while a second dilatation balloon 806b is provided at the second distal end 804b. The catheter body 802 further comprises a central portion 808, and inflation ports 810a and 810b are provided along the central portion 808. A connector 116 is slidably positioned along the central portion 808 and operates in the manner described above.

Referring specifically to FIGS. 21 and 22, the structure of the catheter assembly 800, and in particular the central portion, is substantially similar to that of the catheter assembly 100 shown in FIGS. 2–5. However, the "fixed-wire" catheter assembly 800 does not have any guidewire lumens; instead, the ends 856a and 856b have guidewires 814a and 814b attached thereto, respectively. Specifically, the guidewire 814a is bonded to the inner hypo-tube 822 at the location 888 by conventional bonding means, such as welding, soldering, laser bonding, or other conventional methods. The guidewire 814b is attached to the seal 848. Each guidewire 814a, 814b extends through the respective distal opening 840a, 840b. Thus, the guidewires 814a and 814b are fixed to the inner hypo-tube 822 and are part of the entire catheter assembly 800.

In operation, the first distal end 804a is inserted into the patient's artery and advanced to the site of the stenosis. When a new balloon is needed, the entire first distal end 804a, including the guidewire 814a, must be withdrawn before the second distal end 804b can be inserted and advanced to the site of the stenosis, which is the standard procedure for any fixed-wire catheter.

5. Dimensions and Materials

Along these lines, exemplary non-limiting dimensions for the balloon catheter assemblies of the present invention may be as follows. The dimensions are provided for the embodiment of FIGS. 2–5, although those skilled in the art will appreciate that similar dimensions are applicable for the other embodiments.

For example, the overall length of the double balloon catheter assemblies will typically range from 170 cm to 175 cm. The inner hypo-tube 122 has an inner diameter of about 0.017 inches and an outer diameter of about 0.023 inches. The outer hypo-tube 120 has an inner diameter of about 0.034 inches and an outer diameter of about 0.040 inches. The length of the outer hypo-tube 120 is about 105 cm, while the length of each distal catheter body 126a or 126b is about 33 cm. The outer diameter of the distal catheter bodies 126a and 126b is about 2.5 French (about 0.0825 cm). The guidewires used in the rapid-exchange embodiments are preferably of a standard length of 175 cm.

Thus, the double balloon catheter assemblies of the present invention provide two easy-to-use catheter systems on the same catheter assembly. This allows angioplasty and catheter exchange to be performed economically, quickly, and conveniently while retaining all the necessary safety precautions. The economic savings are not insignificant in light of the current demand for lower health care costs, and can be realized from several aspects: the reduced cost of providing one catheter assembly instead of two separate catheters; fewer disposable materials; and less inventory and lower administrative costs for the hospitals.

The principles of the present invention are also broad-based in that they may be applied to all the currently-available types of catheter systems: the "rapid-exchange" system, the "over-the-wire" system, and the "fixed-wire" system.

In closing it is to be understood that the embodiments of the invention disclosed herein are illustrative of the principals of the invention and that other modifications may be employed which are within the scope thereof. For example, it is not necessary that both distal ends of the catheter assembly be provided to operate under the same principles. Specifically, one distal catheter body may provided and configured to operate as an "over-the-wire" catheter while the other distal catheter body may provided and configured to operate as a "rapid-exchange" catheter. Likewise, one distal catheter body may provided and configured to operate as an "over-the-wire" catheter while the other distal catheter body may provided and configured to operate as a "fixed wire" catheter. Any of the combinations between the various "fixed wire" "over-the-wire" and "rapid-exchange" principles may be employed on a single catheter assembly of the present invention without departing from the spirit and scope thereof. Accordingly, the present invention is not limited to that precisely as shown and described in the specification.

What is claimed:

1. A catheter assembly comprising:
    a) an elongated body which includes
        a central section having first and second ends, a first inflation lumen extending to the first end, an a first inflation port in fluid communication with the first inflation lumen, a second inflation lumen extending to the second end, a second inflation port in fluid communication with the second inflation lumen,
        a first extremity connected to the first end of the central portion and having a third inflation lumen extending therein in fluid communication with the first inflation lumen,
        a first balloon on the first extremity having an interior in fluid communication with the third inflation lumen,
        a second extremity connected to the second end of the central portion and having a fourth inflation lumen extending therein in fluid communication with the second inflation lumen, and
        a second balloon on the second extremity having an interior in fluid communication with the fourth inflation lumen; and
    b) a connector element having first and second ends, a first inner lumen which is configured to slidably receive the central section of the elongated body, means on the first and second ends of the connector element to sealingly engage a first portion of the central section of the elongated body on one side of one of the inflation ports in the central section and a second portion of the central section of the elongated body on the opposite side of said one of the inflation ports and a second inner lumen having one end in communication with the first inner lumen and a second end configured to be connected to a source of inflation fluid.

2. The catheter assembly of claim 1, further comprising a protective tubular sheath covering the second extremity and the second end of the central section.

3. The catheter assembly of claim 1, wherein the first extremity and the second extremity each comprises a flexible catheter shaft.

4. The catheter assembly of claim 3 wherein the catheter shaft of the first extremity has a distal end, a first guidewire port in the distal end, a second guidewire port spaced proximally from the balloon on the first extremity and a guidewire passageway extending from the first guidewire port to the second guidewire port.

5. The catheter assembly of claim 4 wherein the guidewire passage is defined by an inner tubular sleeve disposed within the catheter shaft of the first extremity.

6. The catheter assembly of claim 4 wherein the catheter shaft of the second extremity has a distal end, a third guidewire port in the distal end, a fourth guidewire port spaced proximally from the balloon on the second extremity and a second guidewire passageway extending from the third guidewire port to the fourth guidewire port.

7. The catheter assembly of claim 6 wherein the second guidewire passage is defined by an inner tubular sleeve disposed within the catheter shaft of the second extremity.

8. The catheter assembly of claim 1 wherein the central section comprises an outer tubular member and an inner tubular member disposed within the outer tubular member.

9. The catheter assembly of claim 8 wherein the second balloon has a larger inflated diameter than the inflated diameter of the first balloon.

10. The catheter assembly of claim 8 wherein at least one of the inner and outer tubular members is formed of hypotubing.

11. The catheter assembly of claim 8 wherein the inner tubular member and the outer tubular member define the second inflation lumen.

12. The catheter assembly of claim 11 wherein the second inflation port extends through a wall portion of the outer tubular member and is in fluid communication with the second inflation lumen.

13. The catheter assembly of claim 8 wherein the inner tubular member defines the first inflation lumen.

14. The catheter assembly of claim 13 wherein the first inflation port extends through a wall portion of the outer tubular member and a wall portion of the inner tubular member and is in fluid communication only with the first inflation lumen.

* * * * *